United States Patent [19]

Slavin

[11] Patent Number: 4,515,164

[45] Date of Patent: May 7, 1985

[54] DIFFERENTIAL DOPPLER FOR BLOOD FLOW MEASUREMENT

[75] Inventor: Martin J. Slavin, Dix Hills, N.Y.

[73] Assignee: Intech Systems Corp., Hauppauge, N.Y.

[21] Appl. No.: 592,490

[22] Filed: Mar. 23, 1984

[51] Int. Cl.³ ............................................. A61B 10/00
[52] U.S. Cl. ................................................. 128/663
[58] Field of Search ................ 73/861.25, 861.31, 196; 128/660–663

[56] References Cited

U.S. PATENT DOCUMENTS

| Re. 28,686 | 1/1976 | Coulthard | 73/194 E |
|---|---|---|---|
| 3,732,532 | 5/1973 | Flaherty et al. | 73/861.25 X |
| 3,766,517 | 10/1973 | Fahrbach | 340/3 D |
| 3,859,984 | 1/1975 | Langley | 128/661 |
| 3,977,247 | 8/1976 | Hassler | 73/194 A |
| 4,257,275 | 3/1981 | Kurita et al. | 73/861.06 |
| 4,434,669 | 3/1984 | Roberts et al. | 128/663 X |

OTHER PUBLICATIONS

Di Pietro, D. M., "IC's for an Implantable CW Doppler UTS Flowmeter", IEEE Solid State Ckts. Jrnl., vol. 12, #510, 1977, pp. 573–576.
USCI Brochure, "Medsonics Ultrasound Stethoscope", USCI Div. of CR Bond, Inc., Billerica, Mass., Dec. 1974.

Primary Examiner—Kyle L. Howell
Assistant Examiner—Francis J. Jaworski
Attorney, Agent, or Firm—Blum Kaplan Friedman Silberman & Beran

[57] ABSTRACT

A portable apparatus for determining the degree of occlusion in a blood vessel. The apparatus includes a transmitter for producing an ultrasonic signal, a first probe for directing the ultrasonic signal to a first location in a blood vessel and a second probe for directing an ultrasonic signal to a second location in the blood vessel. A first receiver receives the ultrasonic signal after return from contact of blood flowing in the blood vessel at the first location and produces a first received signal representative thereof. A second receiver receives the ultrasonic signal after returning from contact with blood vessel at the second location and produces a second received signal representative thereof. A difference measuring circuit receives the first and second received signals and produces a difference signal representative of the difference between the first and second received signals so that a difference in blood flow velocity at the first and second locations can be determined.

9 Claims, 2 Drawing Figures

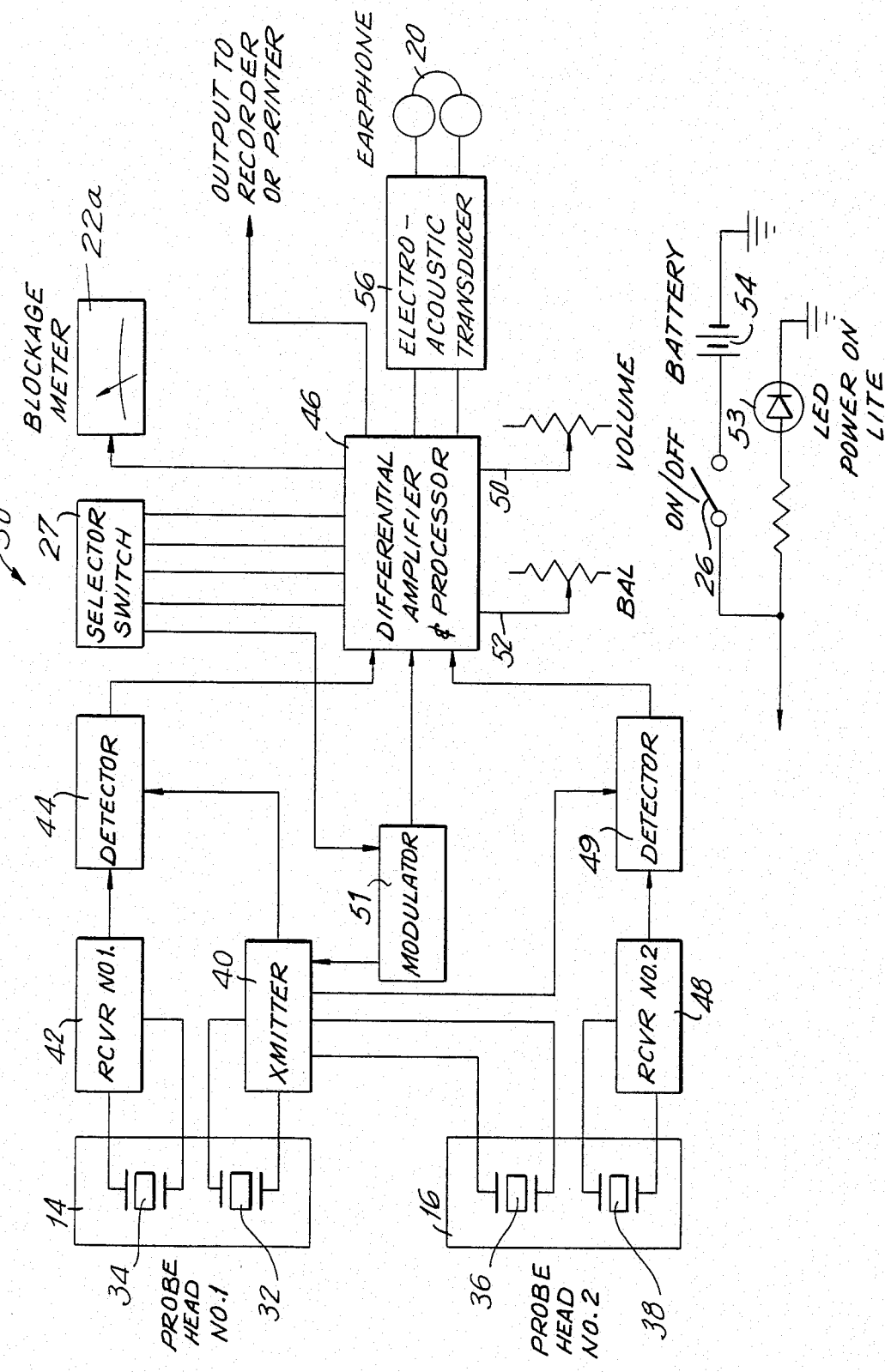

DIFFERENTIAL DOPPLER FOR BLOOD FLOW MEASUREMENT

BACKGROUND OF THE INVENTION

The present invention is directed to an apparatus for measuring blood flow and, in particularly, to an apparatus which can simultaneously determine the difference in blood flow in a blood vessel at spaced locations to determine whether a partial occulsion is present and to pinpoint the location of the occlusion. The apparatus utilizes ultrasonic signals and is non-intrusive.

The Doppler effect has been utilized to provide an indication as to whether blood is flowing in a particular blood vessel. More recent prior art devices utilize the Doppler effect, which provides a change in frequency of waves emitted or reflected from a moving source such as flowing blood, to determine the velocity of flow. Such prior art devices are exemplified by U.S. Pat. Nos. 4,257,275 and Re. 28,686 which utilize two pairs of ultrasonic transducers to measure fluid flow in a vessel at spaced locations. In these patents, the signals transmitted across the fluid between the transducers of each pair are utilized to determine the time delay between the flowing material to provide a single measurement of the fluid flow velocity. Noise, frequency modulation or phase modulation in the transmitter signals are compared. Other arrangements utilizing pairs of transmitters-receivers, as exemplified by U.S. Pat. Nos. 3,977,247 and 3,766,517 provide single measurements of velocity or flow volume by focusing on the same or overlapping volumes.

None of these prior art devices are capable of determining whether an occlusion exists in a blood vessel by utilizing ,the different in blood flow speed measured at two spaced locations based on its Doppler effect. Accordingly, it is desired to ,provide a blood flow measurement apparatus which utilizes the Doppler effect to pinpoint the location of an occlusion in a blood vessel.

SUMMARY OF THE INVENTION

Generally speaking, in accordance with the present invention, an apparatus for determining whether an occlusion is present in a blood vessel is provided. The apparatus includes a transmitter which produces an ultrasonic signal. A first probe directs the ultrasonic signal to a first location in a blood vessel. A second probe directs the ultrasonic signal to a second location in the blood vessel. A first receiver receives the ultrasonic signal after return from contact with blood flowing in the blood vessel at the first location and produces a first received signal representative thereof. A second receiver receives the ultrasonic signal after return from contact with the blood flowing in the blood vessel at the second location and produces a second received signal representative thereof. A difference measuring circuit which may include a differential amplifier produces a difference signal representative of the difference between the first and second received signals whereby a difference in blood flow at the two spaced locations can be determined to pinpoint the location of an occlusion.

In a preferred form of the invention, the required circuitry and probes are provided in a portable, handheld housing. The differential amplifier may produce an audible tone in an earphone coupled to the housing such as in the form of a stethoscope, the frequency of the audible tone being a function of the degree of difference of blood flow velocity between the two probes. The circuitry may also be coupled to a recorder, printer, or an oscilloscope to permit a permanent record of the measurements to be made. Preferably, the unit is operated by a battery to permit complete portability.

Accordingly, it is an object of the present invention to provide an apparatus for determining whether a partial or completed occlusion exists in a blood vessel.

Another object of the present invention is to provide an apparatus which utilizes the Doppler effect to determine the location of an occlusion in a blood vessel.

A further object of the present invention is to provide a portable apparatus which utilizes the Doppler effect to detect the difference in the velocity of blood flow within an area of a selected blood vessel.

Still other objects and advantages of the invention will in part be obvious and will in part be apparent from the specification.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the invention, reference is had to the following description taken in connection with the accompanying drawing, in which:

FIG. 2 is a block circuit diagram of the circuitry utilized in the differential doppler apparatus depicted in FIG. 1.

DESCRIPTION OF THE PREFERRED EMBODIMENT

Figure 1:
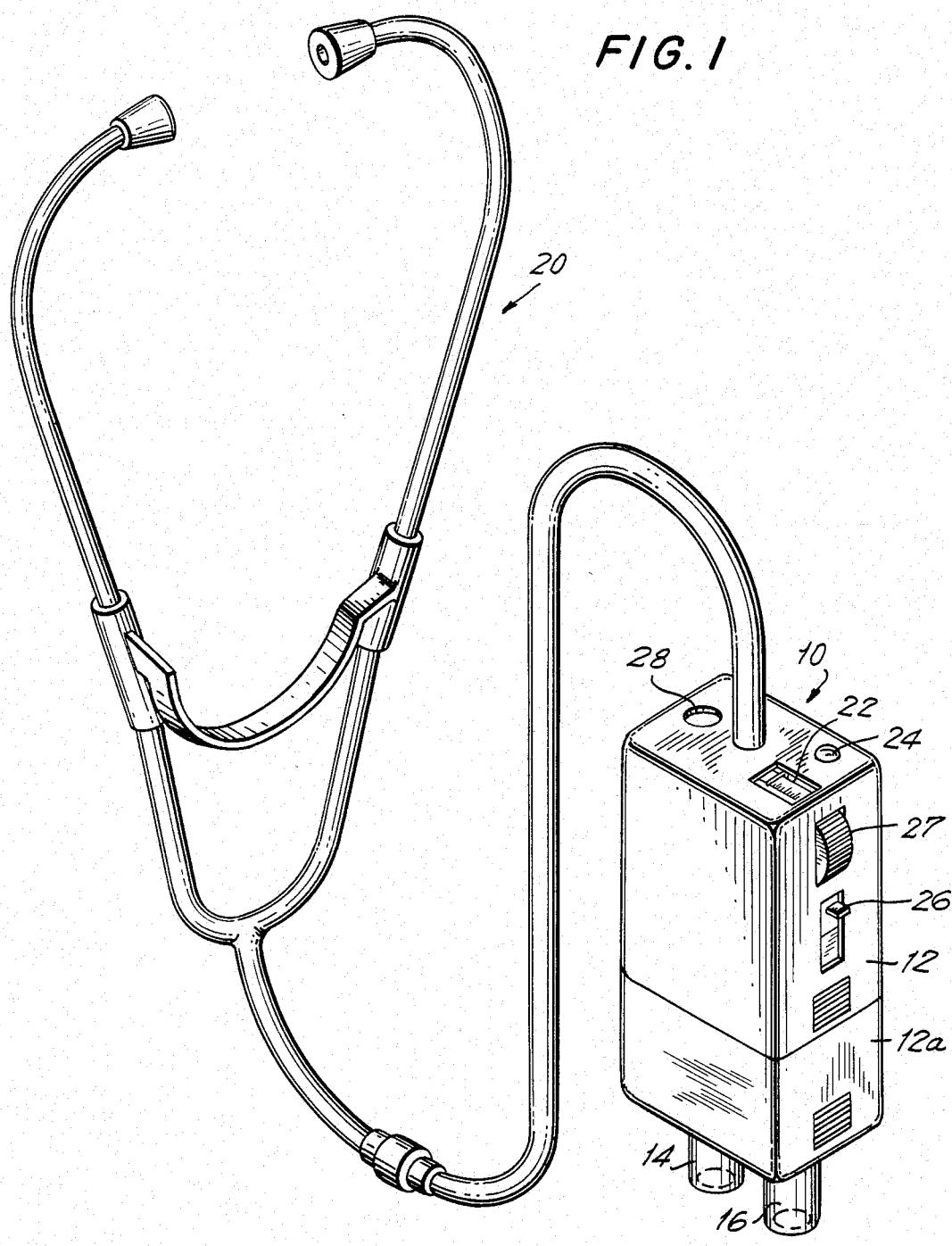
FIG. 1 is a perspective view of a differential doppler apparatus constructed in accordance with a preferred embodiment of the present invention.

Reference is made to FIG. 1 which depicts a differential doppler apparatus, generally indicated at 10, constructed in accordance with a preferred embodiment of the present invention. Apparatus 10 includes a housing 12 having housed therein electronic circuitry 30 (FIG. 2), the construction of which is described below in detail. Housing 12 includes a first probe head 14 and a second probe head 16 spaced a predetermined distance from first probe head 14. Probe heads 14 and 16 are adapted to be moved with housing 12 on the skin surface of a patient along a selected blood vessel. As described more fully below, apparatus 10 may include an earphone set 20, a meter 22, a light indicator such as LED 24, an on-off switch 26, a balance control 27 and a jack 28 to which other measuring or printing devices may be coupled. A battery is removably mounted in housing 12, lower housing portion 12a being removable for this purpose. Additional switches forming a part of selector switch 27 (see FIG. 2) are mounted on the opposed side of housing 12 to the side bearing on-off switch 26 and balance control 27, not seen in FIG. 1.

Referring now to FIG. 2, circuit 30 includes a first transducer 32 and a second transducer 34 positioned in first probe head 14. Positioned in second probe head 16 is a third transducer 36 and a fourth transducer 38. First transducer 32 in first probe head 14 and third transducer 36 in second probe head 16 are coupled to a transmitter 40.

Transmitter 40 causes first and third transducers 32 and 36 to produce ultrasonic signals which are directed through probe heads 14 and 16, respectively towards a selected blood vessel in a patient. Due to the Doppler effect, since blood is flowing in the blood vessel, the frequency of the signal returned or reflected back from the flowing blood will be of a different frequency than the original signal.

The ultrasonic signal produced by first transducer 32, after being acted upon by the flowing blood, will be received by second transducer 34 in first probe head 14. Second transducer 34 is coupled to a first receiver 42 which receives the signal detected by first transducer 34. The signal produced by first receiver 42 is applied to a first detector 44. Detector 44 may be, by way of example, an FM discriminator adapted to compare the frequencies of the received and transmitted signals to produce a signal representative of frequency shift between the two signals, and therefore blood flow speed. The signal thereafter produced by detector 44 is applied to a differential amplifier and processor 46.

Similarly, fourth transducer 38 receives the reflected signal produced by third transducer 36 whose frequency is shifted by the Doppler effect due to the flowing blood. The signal received by fourth transducer 38 is applied to a second receiver 48 whose signal is thereafter applied to a second detector 49, similar to detector 44. The signal produced by second dectector 50 is also applied to differential amplifier and processor 46.

Selector switch 27 is coupled to differential amplifier and processor 46 and a modulator 51 to provide function selection and control. Modulator 51 is coupled between transmitter 40 and differential amplifier and processor 46. Selector switch 27 permits desired selection of sensitivity of the differential amplifier and processor 46, the selection of desired frequencies produced by transmitter 40 through control of modulator 52, the selection of the audio range and nature of the audio signal produced by differential amplifier and processor 46, the gain applied to the signal for blockage meter 22a, as well as the selection of desired operation functions. By way of function, the selector switch selects whether the output of differential amplifier and processor 46 is a difference signal or just a signal of one or the other probes as desired by the operator, as well as whether the modulator should operate.

Differential amplifier and processor 46 produces a signal which is representative of the difference in frequency shift of the signals received by second transducer 34 and fourth transducer 38, the difference in the output of detectors 44 and 49. This difference signal is representative of the difference in speed at the two spaced locations represented by probe heads 14, 16, and therefore of the degree of blockage. The signal produced by differential amplifier and processor 46 may be an audible tone modulated by modulator 51 which is applied to earphone 20, with the nature of the tone being a function of the degree of difference in blood flow velocity between first and second probe heads 14 and 16. A conventional electro-acoustic transducer 56 is provided to produce the audible tone. In addition, an output from differential amplifier and processor 46 may be applied to a recorder, printer, or oscilloscope to permit viewing of the signal and the making of a permanent record of the measurements. Finally, a meter 22 such as blockage meter 22a may receive an output from differential amplifier and processor 46 to provide a visual indication of the degree of blockage or occlusion in the selected blood vessel.

A volume control 50 and balance control 52 may be provided for adjusting the volume and balance of the signal produced by differential amplifier and processor 46. A power on light such as an LED 53 indicates to the operator whether the apparatus is on or off. An on-off switch 26 is also provided.

The apparatus is preferably powered by a battery 54 enclosed within housing 12 to make the device completely portable and usable at any desired location.

In operation, the blood vessel to be examined is located and housing 12 is positioned so that probe heads 14 and 16 are positioned over the selected blood vessel. The output from differential amplifier and processor 46 will provide an indication to the operator whether or not a blockage is present and will measure the degree of blockage or occlusion. In this manner, the beginning of plaque formation or the location of a blood clot, possibly resulting in a major occlusion can be detected in the early stages by the present invention.

The present invention provides a convenient, low-cost, hand-held device suitable for carrying in a doctor's pocket or bag. The doctor can move the apparatus gradually along the surface of the skin over the desired blood vessel to determine whether there is any blockage or occlusion and can precisely pinpoint the location of such occlusion.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. An apparatus for determining whether an occlusion is present in a blood vessel comprising a portable housing, transmitter means supported in said housing for producing an ultrasonic signal of a given frequency, a first probe supported on said housing for directing said ultrasonic signal to a first location in a blood vessel and receiving a reflected ultrasonic signal from said first location, a second probe supported on said housing and spaced a predetermined distance from said first probe for directing said ultrasonic signal to a second location in said blood vessel spaced from said first location and receiving a reflected ultrasonic signal from said second location, said predetermined distance being chosen so that said first probe is responsive substantially to signals from said first location and said second probe is responsive substantially to signals from said second location, first receiver means supported in said housing for receiving said reflected ultrasonic signal after return from contact with blood flowing in said blood vessel at said first location and for producing a first received signal representative of frequency shift of the received signal, second receiver means supported in said housing for receiving said reflected ultrasonic signal after return from contact with blood flowing in said blood vessel at said second location and for producing a second received signal representative of frequency shift of the received signal, and difference measuring means supported in said housing for receiving said first and second received signals and for producing a difference signal representative of a measurement of the difference between said first and second received signals whereby a difference in blood flow velocity is determined.

2. The apparatus as claimed in claim 1, wherein said difference measuring means includes a differential amplifier which receives said first and second received signals and which produces a signal representative of the difference therebetween.

3. The apparatus as claimed in claim 2, wherein the output from said differential amplifier includes an audible tone signal, the frequency of which is a function of the degree of difference in blood flow velocity at said first and second locations.

4. The apparatus as claimed in claim 3, further comprising earphone means for permitting hearing of said audible tone.

5. The apparatus as claimed in claim 4, further comprising meter means for receiving an output signal produced by said differential amplifier for providing a visual indication of the degree of blockage of the blood vessel.

6. The apparatus as claimed in claim 1, wherein said first probe head includes first and second transducers and said second probe head includes third and fourth transducers, said first and third transducers being coupled to said transmitter means, said second transducer being coupled to said first receiver means and said fourth transducer being coupled to said second receiver means.

7. The apparatus as claimed in claim 1 wherein said apparatus is powered by a battery supported in said housing.

8. The apparatus as claimed in claim 1, further including means for connecting an output of said difference measuring means to a recording means for making a record of blood flow.

9. The apparatus as claimed in claim 1, wherein each said receiver means includes an FM discriminator.

* * * * *